United States Patent [19]

Love et al.

[11] 4,159,996
[45] Jul. 3, 1979

[54] PREPARATION OF ALKANE DIAMINES

[75] Inventors: Richard F. Love; Stanley R. Newman, both of Fishkill, N.Y.; John M. Larkin, Austin, Tex.

[73] Assignee: Texaco Inc., New York, N.Y.

[21] Appl. No.: 847,193

[22] Filed: Oct. 31, 1977

[51] Int. Cl.² .................................................. C07C 85/08
[52] U.S. Cl. .................... 260/570.5 P; 260/566 R; 260/566 A; 260/566 P; 260/583 M; 260/583 P; 260/593 A
[58] Field of Search .............. 260/570.5 P, 583 M, 260/583 P, 618 H, 632 R, 566 R, 566 A, 566 F

[56] References Cited

U.S. PATENT DOCUMENTS

| | | | |
|---|---|---|---|
| 1,799,110 | 3/1931 | Manske | 260/566 X |
| 2,746,959 | 5/1956 | Bruce et al. | 260/566 X |
| 3,737,462 | 6/1973 | Cheema et al. | 260/583 |
| 3,772,358 | 11/1973 | Billere | 260/583 X |

OTHER PUBLICATIONS

Beilsteine, "Organischen Chemie", vol. 1, Acyclische Reihe, p. 661 (1918).
Wagner et al., "Synthetic Organic Chemistry", p. 728 (1953).

*Primary Examiner*—Robert V. Hines
*Attorney, Agent, or Firm*—Thomas H. Whaley; Carl G. Ries; George J. Darsa

[57] ABSTRACT

A method for preparing alkane diamines by initially reacting a vicinal nitroketone with a primary amine hydrochloride thereby forming a nitroalkyliminoalkane or a nitrooximinoalkane and thereafter catalytically hydrogenating the nitroalkylimino- or nitrooximinoalkane to a diamine.

25 Claims, No Drawings

PREPARATION OF ALKANE DIAMINES

BACKGROUND OF THE INVENTION

This invention relates to a method of preparing alkane diamines. In particular, it relates to a novel method for preparing the diamines from vicinal nitroketones.

Diamines, such as ethylene diamine, propylene diamine, etc., have long been known and are useful in preparing textile finishing resins, fungicides, herbicides, corrosion inhibitors, petroleum additives and polyamides to name but a few. The diamines can be prepared by, for example, treating ethylene dichloride with ammonia and a mixture of products is generally obtained albeit that reaction conditions can vary. For example, at low temperatures and pressures ethylene diamine is predominantly formed in low yield. When elevated temperatures and pressures are employed, the yield of ethylene diamine is higher, but the amount of polyethylene polyamines formed is likewise greater.

Diamines may also be prepared by reacting a primary or secondary amine and formaldehyde with a nitroparaffin to form a nitroamino intermediate and thereafter hydrogenating the intermediate. Alternately, a nitroolefin and a primary amine may be reacted to form a similar nitroamino intermediate followed by hydrogenating the intermediate. The aforementioned methods are unsuitable for preparing 1,2-diamines inasmuch as each of the nitroamino intermediates are unstable and undergo further reaction or decomposition.

Another method for preparing 1,2-diamines may be by the action of a nitrogen oxide, such as $N_2O_3$ or $N_2O_4$, on olefins at low temperature followed by reduction of the intermediate dinitrocompound. However, the nitration of olefins with nitrogen oxides leads to the formation of complex mixtures including nitronitroso, nitronitrate, nitronitrile, nitroalochol, nitroolefin and dinitrocompounds as well as products of olefin oxidation. Only a fraction of the olefin charged can be converted to dinitro or nitronitroso derivatives and thence to the diamine.

It is therefore an object of this invention to provide a method for the preparation of alkane diamines.

Another object of this invention is to provide a method for the preparation of alkane diamines in high yields.

Yet another object of this invention is to provide a method for the preparation of alkane diamines in the absence of substantial by-product formation.

A further object of this invention is to provide a method for preparing diamines from stable intermediate products.

Other objects and advantages will become apparent from a reading of the following detailed description and examples.

SUMMARY OF THE INVENTION

Broadly, this invention contemplates a method for the preparation of an alkane diamine which comprises contacting a vicinal nitroketone and a primary amine hydrochloride thereby forming a nitroalkyliminoalkane or a nitrooximinoalkane and thereafter catalytically hydrogenating the nitroalkylimino- or nitrooximinoalkane to a diamine.

According to our invention, the vicinal nitroketones employed in the instant method correspond to the formula:

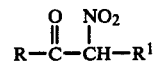

where R is an alkyl group of from 1 to 20 carbon atoms and where $R^1$ is hydrogen or an alkyl group having from 1 to 20 carbon atoms. A combination of groups may be present, as for example, R can be alkyl and $R^1$ hydrogen or R and $R^1$ may both be alkyl. Preferably, the material reacted according to the instant method is a vicinal nitroketone where R is an alkyl group and $R^1$ is hydrogen.

Illustrative of the nitroketones contemplated herein can be mentioned 1-nitro-2-propanone, 1-nitro-2-butanone, 3-nitro-2-butanone, 2-nitro-3-pentanone, 1-nitro-2-pentanone, 3-nitro-2-pentanone, 1-nitro-2-hexanone, 3-nitro-2-hexanone, 4-nitro-3-hexanone, 1-nitro-2-heptanone, 3-nitro-4-heptanone, 5-nitro-4-octanone, 1-nitro-2-decanone, 5-nitro-4-dodecanone, 3-nitro-4-pentadecanone, 1-nitro-2-hexadecanone, 9-nitro-8-heptadecanone, 1-nitro-2-octadecanone, 5-nitro-6-eicosanone and 1-nitro-2-heneicosanone.

More particularly, the method of this invention comprises reacting under the conditions specified herein, a nitroketone as hereinabove recited with a primary amine hydrochloride corresponding to the formula:

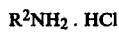

where $R^2$ is an alkyl group of from 1 to 12 carbons or an aryl group of from 6 to 12 carbons or aralkyl group of from 7 to 12 carbons or a hydroxyl group. Illustrative of the primary amine hydrochlorides contemplated in the instant method, we mention methylamine hydrochloride, ethylamine hydrochloride, propylamine hydrochloride, n-butylamine hydrochloride, hexylamine hydrochloride, octylamine hydrochloride, decylamine hydrochloride, dodecylamine hydrochloride, aniline hydrochloride, m-methylaniline hydrochloride, p-ethylaniline hydrochloride, p-tertiarybutylaniline hydrochloride, benzylamine hydrochloride and hydroxylamine hydrochloride. Preferred primary amine hydrochlorides are hydroxylamine hydrochloride, n-butylamine hydrochloride, aniline hydrochloride and benzylamine hydrochloride.

In the practice of the present method, the nitroketone is contacted with the primary amine hydrochloride in amounts ranging from about 1 to 3, preferably from 1 to 1.5, moles of primary amine hydrochloride per mole of nitroketone. Moreover, the contacting is conducted at a temperature of from about 20° to 150° C., preferably 50° to 120° C., and at pressures ranging from atmospheric to 1000 p.s.i.g. The reaction time is normally between about 3 to 16 hours, although longer or shorter periods may be employed depending upon the reaction temperature. Further, the contacting of the nitroketone and primary amine hydrochloride can be conducted in the presence of a solvent not adversely affecting the reaction. While excess primary amine hydrochlorides can function as the reaction medium, non-aqueous solvents can be satisfactorily employed. The reaction can be conveniently undertaken in the presence of a polar non-protic diluent, suitably an oxygenated solvent, such as dioxane, diethylether, tetrahydrofuran, methylethylglycol ethers or 1,2-dimethoxyethane. Suitably, the solvent, when employed, has a boiling point of about 50° to 200° C. A tertiary amine in the liquid phase under the reaction conditions outlined above can additionally be present and typical amines contemplated include pyridine, quinoline and tributylamine.

At the completion of the reaction, the product comprises a nitroalkyliminoalkane or a nitrooximinoalkane corresponding to the formula:

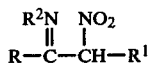

where R, $R^1$ and $R^2$ are as heretofore defined and illustrated by such compounds as 1-nitro-2-oximinopropane, 1-nitro-2-oximinobutane, 1-nitro-2-oximinopentane, 2-nitro-3-oximinopentane, 1-nitro-2-n-butyliminohexane, 4-nitro-3-propyliminohexane, 3-nitro-4-oximinoheptane, 5-nitro-4-octyliminooctane, 1-nitro-2-oximinodecane, 1-nitro-2-n-butyliminodecane, 1-nitro-2-phenyliminodecane, 5-nitro-4-hexyliminododecane, 3-nitro-4-octyliminopentadecane and 1-nitro-2-benzyliminohexadecane.

The nitroalkyliminoalkanes or nitrooximinoalkanes prepared above may be recovered, if desired, by such conventional means as distillation or crystallization.

Subsequently, the nitroalkyliminoalkanes or nitrooximinoalkanes prepared as described above are converted to alkane diamines in quantitative yield by catalytic hydrogenation in an alcoholic medium in the presence of a conventional hydrogenation catalyst at temperatures ranging from about 20° to 120° C., preferably from 20° to 100° C. under hydrogen pressures ranging from about 1 to 30 atmospheres of hydrogen and preferably between 1 and 10 atmospheres of hydrogen.

In general, any well-known or conventional hydrogenation catalyst may be employed in this stage of the overall method, including activated nickel and cobalt. Noble metal hydrogenation catalysts can likewise be employed including rhodium, palladium and platinum. The catalyst may be employed as finely divided or precipitated metal, metal oxide or salt, such as platinum oxide, palladium dichloride, rhodium oxide, rhodium trichloride, platinum and palladium. Preferably, we employ platinum, palladium or nickel hydrogenation catalysts. The hydrogenation catalysts may be unsupported or the metal component may be present on a support, such as alumina, silica, carbon or kieselguhr.

Alcoholic media employed in this step include liquid alkanols, such as methanol, ethanol, propanol, isopropanol, butanol, hexanol, octanol, isooctanol, and dodecanol. Alcohols having 1 to 8 carbons are preferably employed.

The alkane diamines prepared pursuant to the method described above correspond to the formula:

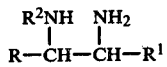

where R, $R^1$ and $R^2$ are as heretofore defined. Representative diamines include, for example, 1,2-diaminopropane, 1,2-diaminobutane, 1,2-diaminopentane, 2,3-diaminopentane, 2-amino-3-propylaminopentane, 1-amino-2-n-butylaminohexane, 3-propylamino-4-aminohexane, 3,4-diaminoheptane, 4-octylamino-5-aminooctane, 1,2-diaminodecane, 1-amino-2-n-butylaminodecane, 1-amino-2phenylaminodecane, 4-hexylamino-5-aminododecane, 3-amino-4-octylaminopentadecane, 1-amino-2-benzylaminohexadecene.

The alkane diamine is thereafter recovered by standard recovery procedures. Suitably, the catalyst can be recovered from the reaction medium by filtration and the alcoholic medium separated by distillation. Inasmuch as the conversion of nitro compound by catalytic hydrogenation is essentially quantitative, the diamine product is of high quality and purity. The diamines can be employed in preparing corrosion inhibitors, such as those described in U.S. Pat. No. 2,848,414, in the control of slime formation as in U.S. Pat. No. 2,878,155 and as mineral flotation or asphalt emulsification agents.

In order to more fully illustrate the nature of this invention and the manner of practicing the same, the following examples are presented.

EXAMPLE 1

A solution of 2.0 grams (10 mmoles) of 1-nitro-2-decanone, 1.0 gram (14.3 mmoles) of hydroxylamine hydrochloride, 5 milliliters of pyridine and 10 milliliters of dioxane was refluxed for 3 hours at 82° C. After separating dioxane by evaporation, the residue was water washed and extracted in ether. An amber colored oil, 1.9 grams, corresponding to an 88 percent yield, was recovered and identified by infrared and nuclear magnetic resonance spectroscopy to be 1-nitro-2-oximinodecane.

The example was repeated except that 10 grams (50 mmoles) of 1-nitro-2-decanone, 5 grams (71.5 mmoles) of hydroxylamine hydrochloride, 20 milliliters of pyridine and 50 milliliters of dioxane were employed. 10 grams of product (89 percent yield) of 1-nitro-2-oximinodecane was recovered.

EXAMPLE 2

A solution of 9.0 grams (4.2 mmoles) of 1-nitro-2-oximinodecane in 350 milliliters (87 moles) of methanol containing 2 grams of a Raney nickel catalyst was hydrogenated at 55 p.s.i.g. of hydrogen for 8 hours. Subsequently, the catalyst was separated by filtration and the solvent stripped. An oily material weighing 6.1 grams (85 percent yield) was recovered and was determined to have a boiling point of 125°–128° C./5mm. Infrared and nuclear magnetic resonance spectroscopy identified the product as 1,2-diaminodecane.

EXAMPLE 3

A blend of 20.1 grams (100 mmoles) of 1-nitro-2-decanone, 15 grams (137 mmoles) of n-butylamine hydrochloride, 50 milliliters (0.62 mole) of pyridine and 100 milliliters of dioxane were refluxed for 8 hours. The solution was thereafter stripped under reduced pressure, the residue diluted with water and extracted with ether. After treatment with aqueous sodium bicarbonate, the ether solution was dried and stripped. 25.6 grams (100 percent crude yield) was recovered, distilled and the fraction (13.1 grams) boiling at 170° C./1mm. collected. The product was identified as 1-nitro-2-n-butyliminodecane. The infrared and nuclear magnetic resonance spectroscopic analyses suggests that the compound exists in the form of an internally hydrogen bonded nitronic acid.

EXAMPLE 4

2.0 grams (7.8 mmoles) of 1-nitro-2-n-butyliminodecane in 50 milliliters of methanol containing 0.2 grams of platinum oxide catalyst was hydrogenated under 60 p.s.i.g. of hydrogen at 60° to 70° C. for a period of 16 hours. After filtering the solution free of catalyst and stripping the solvent, an oily residue weighing 1.61 grams (90 percent yield) was identified as 1-amino-2-n-butylaminodecane basis infrared analysis.

EXAMPLE 5

A solution of 7.1 grams (25 mmoles) of 1-nitro-2-hexadecanone, 3.8 grams (25 mmoles) of benzylamine hydrochloride, 15 millilliters (186 mmoles) of pyridine and 50 millilliters of dioxane was refluxed for 8 hours. The solvent was thereafter stripped under reduced pressure and the residue taken up in 200 millilliters of ether and repreatedly washed with water. After drying, the ether was stripped and 8.1 grams of a tan powder was recovered. Recrystallization of the powder from petroleum ether afforded 1.25 grams of unreacted nitroketone and 6.95 grams (73 percent yield) of crystalline material identified by infrared and nuclear magnetic resonance spectroscopy as 1-nitro-2-benzyliminohexadecane.

EXAMPLE 6

A solution of 20.1 grams (100 mmoles) of 1-nitro-2-decanone, 13.0 grams (100 mmoles) of aniline hydrochloride, 50 millilliters (0.62 mole) of pyridine and 100 millilliters of dioxane was refluxed for 5 hours. The solution was then stripped of solvent and the residue diluted with 300 millilliters of water and extracted with ether. The ether solution was thereafter washed with 400 millilliters of 10 percent HCl solution, followed by 200 millilliters of 50 percent saturated sodium bicarbonate solution. After water washing, the ether solution was dried, diluted with pentane, the pentane evaporated and two fractions were recovered. One fraction consisted of 2.5 grams of unreacted nitroketone and the other fraction of 23.5 grams (86 percent yield) of a dark oil was identified by infrared to be 1-nitro-2-phenyliminodecane.

We claim:

1. A method for the preparation of an alkane diamine which comprises contacting a vicinal nitroketone corresponding to the formula:

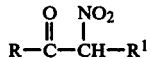

where R is an alkyl group of from 1 to 20 carbon atoms and where $R^1$ is hydrogen or an alkyl group having 1 to 20 carbon atoms and a primary amine hydrochloride thereby forming a nitroalkyliminoalkane or a nitrooximinoalkane and thereafter catalytically hydrogenating said nitroalkyliminoalkane or said nitrooximinoalkane.

2. A method according to claim 1 wherein said contacting is conducted at from about 20° to 150° C.

3. A method according to claim 1 wherein said contacting is conducted at from about 50° to 120° C.

4. A method according to claim 1 wherein the mole ratio of said nitroketone to said hydrochloride is from about 1:1 to 1:3.

5. A method according to claim 1 wherein said hydrochloride is hydroxyl amine hydrochloride.

6. A method according to claim 1 wherein said hydrochloride is n-butylamine hydrochloride.

7. A method according to claim 1 wherein said hydrochloride is aniline hydrochloride.

8. A method according to claim 1 wherein said hydrochloride is benzylamine hydrochloride.

9. A method according to claim 1 wherein said hydrogenating is conducted at from about 20° to 120° C.

10. A method according to claim 1 wherein said hydrogenating is conducted in the presence of a platinum catalyst.

11. A method according to claim 1 wherein said hydrogenating is conducted in the presence of a nickel catalyst.

12. A method according to claim 1 wherein said diamine is 1,2-diaminodecane.

13. A method according to claim 1 wherein said diamine is 1-amino-2-n-butylaminodecane.

14. A method for the preparation of a nitrooximinoalkane or a nitroalkyliminoalkane which comprises contacting a vicinal nitroketone corresponding to the formula:

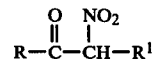

where R is an alkyl group of from 1 to 20 carbon atoms and where $R^1$ is hydrogen or an alkyl group having 1 to 20 carbon atoms and a primary amine hydrochloride.

15. A method according to claim 14 wherein said contacting is conducted at from about 20° to 150° C.

16. A method according to claim 14 wherein said contacting is conducted at from about 50° to 120° C.

17. A method according to claim 14 wherein the mole ratio of said nitroketone to said hydrochloride is from about 1:1 to 1:3.

18. A method according to claim 14 wherein said hydrochloride is hydroxyl amine hydrochloride.

19. A method according to claim 14 wherein said hydrochloride is n-butylamine hydrochloride.

20. A method according to claim 14 wherein said hydrochloride is aniline hydrochloride.

21. A method according to claim 14 wherein said hydrochloride is benzylamine hydrochloride.

22. A method according to claim 14 wherein said oximinoalkane is 1-nitro-2-oximinodecane.

23. A method according to claim 14 wherein said iminoalkane is 1-nitro-2-n-butyliminodecane.

24. A method according to claim 14 wherein said iminoalkane is 1-nitro-2-n-benzyliminohexadecane.

25. A method according to claim 14 wherein said iminoalkane is 1-nitro-2-phenyliminodecane.

* * * * *